United States Patent [19]

Henrick et al.

[11] 4,200,758

[45] Apr. 29, 1980

[54] 2,4-IMIDAZOLIDINEDIONYLMETHYL ESTERS AND THIOLESTERS OF ANILINO ACIDS

[75] Inventors: Clive A. Henrick, Palo Alto; Gustave K. Kohn, Berkeley, both of Calif.

[73] Assignee: Zoecon Corporation, Palo Alto, Calif.

[21] Appl. No.: 21,666

[22] Filed: Mar. 19, 1979

[51] Int. Cl.$^2$ .......................................... C07D 233/72
[52] U.S. Cl. .............................. 548/312; 424/273 R; 548/307
[58] Field of Search .......................... 548/309, 312

[56] References Cited

U.S. PATENT DOCUMENTS

| 3,676,454 | 7/1972 | Vida | 548/312 |
| 3,864,357 | 2/1975 | Porret et al. | 548/312 |
| 4,028,378 | 6/1977 | MacFadyen | 548/312 |
| 4,112,233 | 9/1978 | Morgan | 548/312 |

FOREIGN PATENT DOCUMENTS

| 38-19990 | 9/1963 | Japan | 548/312 |
| 995864 | 6/1965 | United Kingdom | 548/312 |

*Primary Examiner*—Natalie Trousof
*Attorney, Agent, or Firm*—Donald W. Erickson

[57] ABSTRACT

2,4-Imidazolidinedionylmethyl esters and thiolesters of amino acids, intermediates therefor, synthesis thereof and the use of said esters and thiolesters and compositions for the control of pests.

38 Claims, No Drawings

2,4-IMIDAZOLIDINEDIONYLMETHYL ESTERS AND THIOLESTERS OF ANILINO ACIDS

This invention relates to novel esters and thiolesters of α-substituted acids, novel intermediates therefor, synthesis thereof, and the control of pests.

The esters and thiolesters of the present invention are represented by the following formula (A):

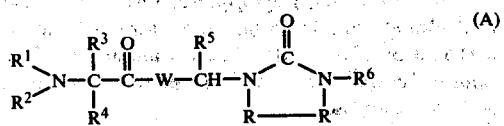

wherein,
one of R and R' is carbonyl and the other is methylene or lower alkylmethylene;
W is oxygen or sulfur;
$R^1$ is cycloalkyl, cycloalkenyl, cycloalkenyl substituted with halo or lower alkyl, or the group

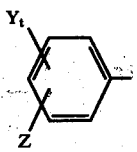

in which t is zero, one, two, three or four; Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and Z is independently selected from the values of Y, cycloalkyl, and lower haloalkoxy; or Y and Z form a methylenedioxy group;
$R^2$ is hydrogen, lower alkyl, lower haloalkylcarbonyl, or formyl; $R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms; $R^4$ is hydrogen or fluoro; $R^5$ is hydrogen, methyl, ethyl, cyano or ethynyl; and
$R^6$ is hydrogen, lower alkyl, lower alkenyl or lower alkynyl. The salt of (A) of a strong inorganic acid or organic acid is included herein.

The compounds of the present invention represented by formula (A) are useful agents for the control of pests such as insects and acarids.

In the description hereinafter and the appended claims, each of R through $R^6$, W, Y, Z, and t is as defined hereinabove, unless otherwise specified.

The compounds of formula (A) can be synthesized as outlined below.

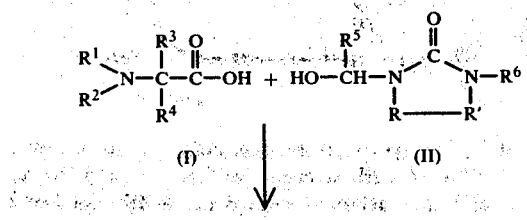

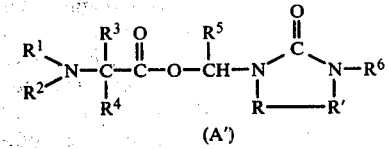

In the general practice of the above synthesis, an acid, salt thereof or the acid chloride is reacted with an alcohol of formula II to form the carboxylic ester A'. For example, an acid chloride of the acid of formula I is reacted with an alcohol of formula II in an organic solvent such as diethyl ether in the presence of triethylamine. In another embodiment, an acid of formula I and an alcohol of formula II are reacted in an organic solvent such as methylene chloride in the presence of 4-dimethylaminopyridine and dicyclohexylcarbodiimide to form an ester of formula A'. In another embodiment, the esters of formula A' are synthesized by reaction of an acid of formula I with phosgene in the presence of an ether such as 1,4-dioxane to form the corresponding oxazolidine-2,5-dione, which is then reacted with an alcohol of formula II to make the corresponding ester of formula A'. In another synthesis, the acid of formula I or salt thereof is reacted with the bromide, chloride or mesylate of the alcohol of formula II to form an ester of formula A'. The starting materials of formula I are described by Henrick and Garcia, Offenlegungsschrift No. 28 12 169. The alcohols of formula II can be made as described in Offenlegungsschrift No. 28 26 864 and references cited therein.

In another embodiment, the compounds of formula (A) can be prepared by the reaction of an amine (III) with an α-halo ester of formula IV (X is bromo or chloro).

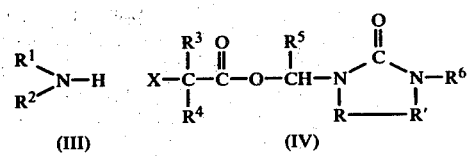

The reaction of an amine (III) and halo ester (IV) is generally carried out neat or in an organic solvent such as hexamethylphosphoric triamide, tetrahydrofuran, dimethylformamide, dimethylsulfoxide, or the like. The halo esters of formula IV can be prepared by reaction of an acid halide thereof with an alcohol of formula II.

The thiolesters of formula (A) can be prepared by the reaction of, for example, the sodium salt of a thioacid corresponding to formula I with the bromide or mesylate of the alcohol of formula II.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to six carbon atoms. The term "lower haloalkenyloxy" refers to a lower alkenyloxy group substituted with one to three halogen atoms.

The term "lower alkynyl" refers to an alkynyl group, straight or branched, having a chain length of two to six carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to six carbon atoms.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such as cyclopropanemethyl, cyclobutaneethyl, cyclohexanemethyl, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

Included within the present invention are salts of the compounds of formula A. The salts are formed from strong inorganic acids or organic acids such as hydrochloric acid, sulfuric acid, phosphoric acid, p-toluenesulfonic acid, benzenesulfonic acid, methanesulfonic acid, and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The compounds of the present invention are further illustrated and defined as follows:

A compound of formula (2):

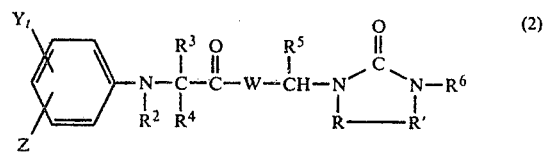

A compound of formula (3):

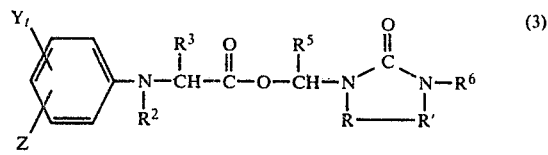

A compound according to formula 3 wherein $R^2$ is hydrogen or methyl.

A compound according to formula 3 wherein $R^2$ is hydrogen or methyl and $R^5$ is hydrogen.

A compound of formula (6):

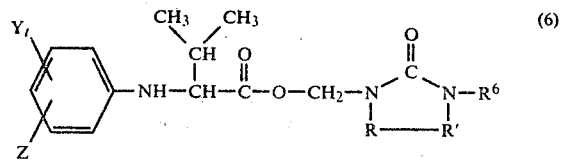

A compound according to formula 6 wherein Z is hydrogen and t is one.

A compound of formula (8):

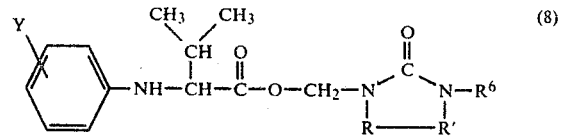

in which Y is hydrogen, bromo, chloro, fluoro, lower alkyl of 1 to 4 carbon atoms, trifluoromethyl, lower alkoxy of 1 or 2 carbon atoms, lower alkylthio of 1 or 2 carbon atoms, lower alkylcarbonyl of 2 or 3 carbon atoms or lower alkoxycarbonyl of 2 to 4 carbon atoms.

A compound according to formula 8 wherein R' is methylene.

A compound according to formula 8 wherein R' is methylene and R⁶ is propargyl.

A compound according to formula 8 wherein R' is ethylidene.

A compound according to formula 8 wherein R' is ethylidene and R⁶ is propargyl.

A compound according to formula 8 wherein Y is in the para position and R' is methylene.

A compound according to formula 8 wherein Y is in the para position, R' is methylene, and R⁶ is propargyl.

A compound according to formula 8 wherein Y is in the para position and R' is ethylidene.

A compound according to formula 8 wherein Y is in the para position, R' is ethylidene, and R⁶ is propargyl.

A compound according to formula 8 wherein Y is bromo, chloro, fluoro, methyl or trifluoromethyl; Y is in the para position; R' is methylene; and R⁶ is propargyl.

A compound according to formula 6 wherein Y is hydrogen, bromo, chloro, fluoro, lower alkyl of 1 to 4 carbon atoms, trifluoromethyl, lower alkoxy of 1 or 2 carbon atoms, lower alkylthio of 1 or 2 carbon atoms, lower alkylcarbonyl of 2 or 3 carbon atoms or lower alkoxycarbonyl of 2 to 4 carbon atoms; Z is cyclopropyl or independently selected from the values of Y; and t is zero or one.

A compound of formula (19):

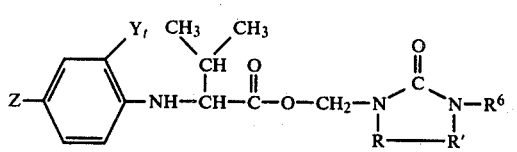

in which t is one; Y is hydrogen, bromo, chloro, fluoro, lower alkyl of 1 to 4 carbon atoms, trifluoromethyl, lower alkoxy of 1 or 2 carbon atoms, lower alkylthio of 1 or 2 carbon atoms, lower alkylcarbonyl of 2 or 3 carbon atoms, or lower alkoxycarbonyl of 2 to 4 carbon atoms; and Z is cyclopropyl or independently selected from the values of Y.

A compound according to formula 19 wherein Y is chloro, fluoro or methyl and Z is bromo, chloro, fluoro, methyl or trifluoromethyl.

A compound according to formula 19 wherein R' is methylene; Y is chloro, fluoro or methyl; and Z is bromo, chloro, fluoro, methyl or trifluoromethyl.

A compound according to formula 19 wherein R' is methylene; R⁶ is propargyl; Y is chloro, fluoro or methyl; and Z is bromo, chloro, fluoro, methyl or trifluoromethyl.

A compound according to formula 19 wherein R' is ethylidene; Y is chloro, fluoro or methyl; and Z is bromo, chloro, fluoro, methyl or trifluoromethyl.

A compound according to formula 19 wherein R' is ethylidene; R⁶ is propargyl; Y is chloro, fluoro or methyl; and Z is bromo, chloro, fluoro, methyl or trifluoromethyl.

A compound according to formula 19 wherein Z is trifluoromethyl, Y is chloro or fluoro, R' is methylene, and R⁶ is propargyl.

A compound according to formula 19 wherein Z is trifluoromethyl, Y is chloro or fluoro, R' is ethylidene, and R⁶ is propargyl.

A compound of formula (27):

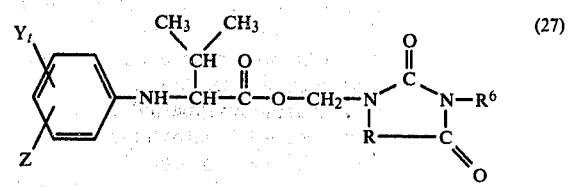

A compound according to formula 27 wherein Y is bromo, chloro, fluoro, methyl or trifluoromethyl.

A compound of formula (29):

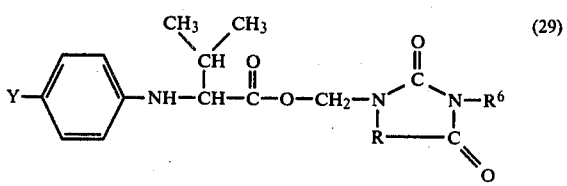

in which Y is bromo, chloro, fluoro, methyl or trifluoromethyl.

A compound according to formula 29 wherein R is methylene.

A compound according to formula 29 wherein R is methylene and R⁶ is propargyl.

A compound according to formula 29 wherein R is ethylidene.

A compound according to formula 29 wherein R is ethylidene and R⁶ is propargyl.

A compound according to formula 27 wherein t is zero or one; Z is hydrogen, bromo, chloro, fluoro, methyl or trifluoromethyl; and Y is bromo, chloro, fluoro, methyl or trifluoromethyl.

A compound of formula (35):

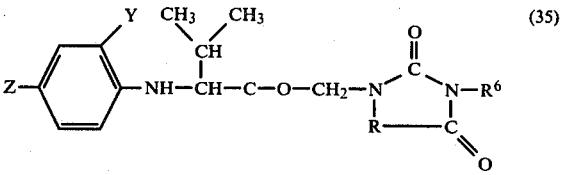

in which Y is bromo, chloro, fluoro, methyl or trifluoromethyl and Z is hydrogen, bromo, chloro, fluoro, methyl or trifluoromethyl.

A compound according to formula 35 wherein R is methylene.

A compound according to formula 35 wherein R⁶ is propargyl and R is methylene.

A compound according to formula 35 wherein R is ethylidene.

A compound according to formula 35 wherein R⁶ is propargyl and R is ethylidene.

The following examples are provided to illustrate the practice of the present invention. Temperature is given in degrees Centigrade. RT means room temperature.

EXAMPLE 1

To a stirred solution of (2,4-dioxo-1-propargyl-3-imidazolidinyl)methanol (0.99 mmol) and triethylamine (1.38 mmol) in ether (about 15 ml), under nitrogen, is added by syringe a solution of the acid chloride of 2-(2-chloro-4-trifluoromethylphenylamino)-3-methylbutanoic acid (1.5 mmol) in ether. The mixture is stirred for 30 minutes and then quenched with saturated aqueous sodium bicarbonate. The ether phase is washed with aqueous sodium bicarbonate, water and brine and filtered through silica. Evaporation of solvent, followed by thin layer chromatography using a circular chromatograph, eluting with 20% ether/hexane, gives (2,4-dioxo-1-propargyl-3-imidazolidinyl)methyl 2-(2-chloro-4-trifluoromethylphenylamino)-3-methylbutanoate.

The above procedure is repeated using (2,4-dioxo-5-ethyl-1-propargyl-3-imidazolidinyl)methanol to give (2,4-dioxo-5-ethyl-1-propargyl-3-imidazolidinyl)methyl 2-(2-chloro-4-trifluoromethylphenylamino)-3-methylbutanoate.

The acid chloride is prepared by the reaction of 2-(2-chloro-4-trifluoromethylphenylamino)-3-methylbutanoic acid with phosgene in ether in the presence of a small amount of dimethylformamide.

EXAMPLE 2

A. To a solution of 2,4-dioxo-1-propargyl-3-imidazolidine-carbaldehyde (1.8 mmol) in 25 ml of ether is added 25 ml of water followed by sodium cyanide (3.04 mmol). The mixture is stirred vigorously while a solution of sodium bisulfite (2.45 mmol) in 15 ml of water is added over about 5 minutes. The reaction mixture is stirred for two hours. The organic phase is separated, washed with water, dried over calcium sulfate and solvent evaporated to give cyano(2,4-dioxo-1-propargyl-3-imidazolidinyl)methanol.

B. To the acid chloride of 2-(2-fluoro-4-trifluoromethylphenylamino)-3-methylbutanoic acid (2.5 mmol) in ether is added 1.3 ml of triethylamine followed by the cyano(2,4-dioxo-1-propargyl-3-imidazolidinyl)methanol in 5 ml of ether, from part A above, over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with 20% ether/hexane to give cyano(2,4-dioxo-1-propargyl-3-imidazolidinyl)methyl 2-(2-fluoro-4-trifluoromethylphenylamino)-3-methylbutanoate. (A', R is carbonyl, R' is methylene, $R^1=R^4$ is hydrogen, $R^2$ is 2-fluoro-4-trifluoromethylphenyl, $R^3$ is isopropyl, $R^5$ is cyano, $R^6$ is 2-propynyl).

EXAMPLE 3

To a stirred solution of (2,4-dioxo-5-methyl-1-propargyl-3-imidazolidinyl)methanol (1.8 mmol), N-(2-chloro-4-trifluoromethylphenyl)valine (2.0 mmol) and dimethylaminopyridine (0.65 mmol) in 20 ml of methylene chloride and 2 ml of dimethylformamide is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph, eluting with 25% ether/hexane, to yield (2,4-dioxo-5-methyl-1-propargyl-3-imidazolidinyl)methyl 2-(2-chloro-4-trifluoromethylphenylamino)-3-methylbutanoate.

EXAMPLE 4

To a solution of 3-(4-chlorophenyl)-4-isopropyloxazolidine-2,5-dione (1.32 mmol) and dimethylaminopyridine in 5 ml of dry tetrahydrofuran is added a solution of (2,4-dioxo-1-propargyl-3-imidazolidinyl)methanol (1.26 mmol) in 3 ml of dry tetrahydrofuran. The reaction mixture is stirred for about 20 hours, under dry air, and then diluted with ether followed by washing with saturated aqueous sodium bicarbonate, water and saturated aqueous sodium chloride. After drying over calcium sulfate, solvent is evaporated. The crude product is chromatographed on a rotary chromatograph eluting with 15% ether/hexane to give (2,4-dioxo-1-propargyl-3-imidazolidinyl)methyl 2-(4-chlorophenylamino)-3-methylbutanoate.

Following the above procedure, 3-(4-methylphenyl)-4-isopropyloxazolidine-2,5-dione is reacted with (2,4-dioxo-1-propargyl-3-imidazolidinyl)methanol to give (2,4-dioxo-1-propargyl-3-imidazolidinyl)methyl 2-(4-methylphenylamino)-3-methylbutanoate.

In the same way, 3-(4-trifluoromethylphenyl)-4-isopropyloxazolidine-2,5-dione is reacted with (2,4-dioxo-1-propargyl-3-imidazolidinyl)methanol to give (2,4-dioxo-1-propargyl-3-imidazolidinyl)methyl 2-(4-trifluoromethylphenylamino)-3-methylbutanoate.

EXAMPLE 5

Following the above procedures, each of (2,4-dioxo-3-ethyl-1-imidazolidinyl)methanol, (2,4-dioxo-3-propargyl-1-imidazolidinyl)methanol, (2,4-dioxo-5-methyl-1-propargyl-3-imidazolidinyl)methanol, (2,4-dioxo-5-ethyl-3-propargyl-1-imidazolidinyl)methanol and (2,4-dioxo-5-ethyl-1-propargyl-3-imidazolidinyl)methanol is reacted with the acid chloride of 2-(4-chlorophenylamino)-3-methylbutanoate to yield (2,4-dioxo-3-ethyl-1-imidazolidinyl)methyl 2-(4-chlorophenylamino)-3-methylbutanoate
(2,4-dioxo-3-propargyl-1-imidazolidinyl)methyl 2-(4-chlorophenylamino)-3-methylbutanoate
(2,4-dioxo-5-methyl-1-propargyl-3-imidazolidinyl)methyl 2-(4-chlorophenylamino)-3-methylbutanoate
(2,4-dioxo-5-ethyl-3-propargyl-1-imidazolidinyl)methyl 2-(4-chlorophenylamino)-3-methylbutanoate
(2,4-dioxo-5-ethyl-1-propargyl-3-imidazolidinyl)methyl 2-(4-chlorophenylamino)-3-methylbutanoate

EXAMPLE 6

Using the procedure of Example 1, (2,4-dioxo-5-methyl-1-n-propyl-3-imidazolidinyl)methanol is reacted with the acid chloride of 2-(4-chlorophenylamino)-3-methylbutanoic acid to give (2,4-dioxo-5-methyl-1-n-propyl-3-imidazolidinyl)methyl 2-(4-chlorophenylamino)-3-methylbutanoate (A'; R is carbonyl, R' is ethylidene, $R^1=R^4=R^5$ is hydrogen, $R^2$ is p-chlorophenyl, $R^3$ is isopropyl, $R^6$ is n-propyl).

EXAMPLE 7

Using the procedures hereinabove, each of the acids (or acid chlorides), N-(4-chloro-2-fluorophenyl)valine, N-(3-fluoro-4-methylphenyl)valine, N-(2-fluoro-4-methylphenyl)valine, N-(2,4-dichlorophenyl)valine, N-(4-bromo-2-fluorophenyl)valine, N-(2-fluoro-4-trifluoromethylphenyl)valine, N-(2-chloro-4-methylphenyl) valine, and N-(2-methyl-4-trifluoromethylphenyl)valine is reacted with (2,4-dioxo-1-propargyl-3-imidazolidinyl)methanol to yield the respective ester:

(2,4-dioxo-1-propargyl-3-imidazolidinyl)methyl 2-(4-chloro-2-fluorophenylamino)-3-methylbutanoate
(2,4-dioxo-1-propargyl-3-imidazolidinyl)methyl 2-(3-fluoro-4-methylphenylamino)-3-methylbutanoate
(2,4-dioxo-1-propargyl-3-imidazolidinyl)methyl 2-(2-fluoro-4-methylphenylamino)-3-methylbutanoate
(2,4-dioxo-1-propargyl-3-imidazolidinyl)methyl 2-(2,4-dichlorophenylamino)-3-methylbutanoate
(2,4-dioxo-1-propargyl-3-imidazolidinyl)methyl 2-(4-bromo-2-fluorophenylamino)-3-methylbutanoate
(2,4-dioxo-1-propargyl-3-imidazolidinyl)methyl 2-(2-fluoro-4-trifluoromethylphenylamino)-3-methylbutanoate
(2,4-dioxo-1-propargyl-3-imidazolidinyl)methyl 2-(2-chloro-4-methylphenylamino)-3-methylbutanoate
(2,4-dioxo-1-propargyl-3-imidazolidinyl)methyl 2-(2-methyl-4-trifluoromethylphenylamino)-3-methylbutanoate

EXAMPLE 8

The acid N-(4-fluorophenyl)valine [2-(4-fluorophenylamino)-3-methylbutanoic acid] is reacted with (2,4-dioxo-1,5-dimethyl-3-imidazolidinyl)methanol using the procedure of Example 3 to give (2,4-dioxo-1,5-dimethyl-3-imidazolidinyl) methyl 2-(4-fluorophenylamino)-3-methylbutanoate.

EXAMPLE 9

The alcohol, [2,4-dioxo-1-(2-propenyl)-3-imidazolidinyl] methanol and [2,4-dioxo-1-(2-propenyl)-5-methyl-3-imidazolidinyl] methanol, is reacted with the acid chloride of 2-(2-chloro-4-trifluoromethylphenylamino)-3-methylbutanoic acid to yield [2,4-dioxo-1-(2-propenyl)-3-imidazolidinyl]methyl 2-(2-chloro-4-trifluoromethylphenylamino)methylbutanoate and [2,4-dioxo-1-(2-propenyl)-5-methyl-3-imidazolidinyl]methyl 2-(2-chloro-4-trifluoromethylphenylamino)-3-methylbutanoate.

What is claimed is:

1. A compound of the following formula:

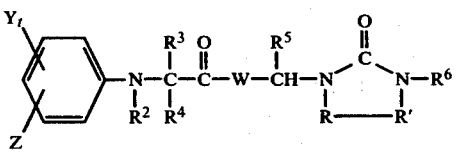

wherein,
one of R and R' is carbonyl and the other is methylene or lower alkylmethylene;
W is oxygen or sulfur;
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
Z is independently selected from the values of Y, cycloalkyl, and lower haloalkoxy; or Z and Y form a methylenedioxy group;
$R^2$ is hydrogen, lower alkyl, lower haloalkylcarbonyl, or formyl;
$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;
$R^4$ is hydrogen or fluoro;
$R^5$ is hydrogen, methyl, ethyl, cyano, or ethynyl; and
$R^6$ is hydrogen, lower alkyl, lower alkenyl or lower alkynyl.

2. A compound according to claim 1 of the formula:

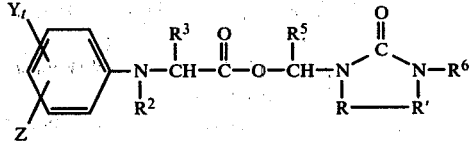

3. A compound according to claim 2 wherein $R^2$ is hydrogen or methyl.

4. A compound according to claim 3 wherein $R^5$ is hydrogen.

5. A compound according to claim 1 of the formula:

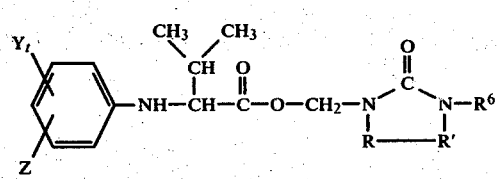

6. A compound according to claim 5 wherein Z is hydrogen, and t is one.

7. A compound according to claim 6 wherein Y is hydrogen, bromo, chloro, fluoro, lower alkyl of 1 to 4 carbon atoms, trifluoromethyl, lower alkoxy of 1 or 2 carbon atoms, lower alkylthio of 1 or 2 carbon atoms, lower alkylcarbonyl of 2 or 3 carbon atoms or lower alkoxycarbonyl of 2 to 4 carbon atoms.

8. A compound according to claim 7 wherein R' is methylene.

9. A compound according to claim 7 wherein R' is methylene and $R^6$ is propargyl.

10. A compound according to claim 7 wherein R' is ethylidene.

11. A compound according to claim 7 wherein R' is ethylidene and $R^6$ is propargyl.

12. A compound according to claim 8 wherein Y is in the para position.

13. A compound according to claim 9 wherein Y is in the para position.

14. A compound according to claim 10 wherein Y is in the para position.

15. A compound according to claim 11 wherein Y is in the para position.

16. A compound according to claim 13 wherein Y is bromo, chloro, fluoro, methyl or trifluoromethyl.

17. A compound according to claim 5 wherein Y is hydrogen, bromo, chloro, fluoro, lower alkyl of 1 to 4 carbon atoms, trifluoromethyl, lower alkoxy of 1 or 2 carbon atoms, lower alkylthio of 1 or 2 carbon atoms, lower alkylcarbonyl of 2 or 3 carbon atoms or lower alkoxycarbonyl of 2 to 4 carbon atoms; Z is cyclopropyl or independently selected from the values of Y; and t is zero or one.

18. A compound according to claim 17 wherein t is one, Y is in the ortho position and Z is in the para position.

19. A compound according to claim 18 wherein Y is chloro, fluoro or methyl and Z is bromo, chloro, fluoro, methyl or trifluoromethyl.

20. A compound according to claim 19 wherein R' is methylene.

21. A compound according to claim 19 wherein R' is methylene and R⁶ is propargyl.

22. A compound according to claim 19 wherein R' is ethylidene.

23. A compound according to claim 19 wherein R' is ethylidene and R⁶ is propargyl.

24. A compound according to claim 21 wherein Z is trifluoromethyl and Y is chloro or fluoro.

25. A compound according to claim 23 wherein Z is trifluoromethyl and Y is chloro or fluoro.

26. A compound according to claim 1 of the formula:

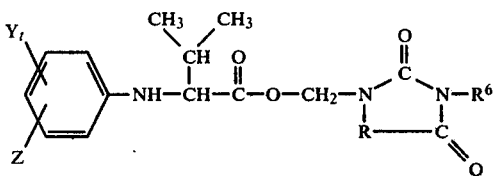

27. A compound according to claim 26 wherein Y is bromo, chloro, fluoro, methyl or trifluoromethyl.

28. A compound according to claim 27 wherein Y is in the para position, Z is hydrogen and t is one.

29. A compound according to claim 28 wherein R is methylene.

30. A compound according to claim 28 wherein R is methylene and R⁶ is propargyl.

31. A compound according to claim 28 wherein R is ethylidene.

32. A compound according to claim 28 wherein R is ethylidene and R⁶ is propargyl.

33. A compound according to claim 27 wherein t is zero or one and Z is hydrogen, bromo, chloro, fluoro, methyl or trifluoromethyl.

34. A compound according to claim 33 wherein Y is in the ortho position, t is one and Z is in the para position.

35. A compound according to claim 34 wherein R is methylene.

36. A compound according to claim 35 wherein R⁶ is propargyl.

37. A compound according to claim 34 wherein R is ethylidene.

38. A compound according to claim 37 wherein R⁶ is propargyl.

* * * * *